United States Patent [19]

Kluger et al.

[11] Patent Number: 5,362,856
[45] Date of Patent: Nov. 8, 1994

[54] MONOOXYGENASE-LIKE ACTIVITY OF HEME PROTEINS

[75] Inventors: Ronald Kluger, Don Mills; Yonghong Song, Toronto, both of Canada

[73] Assignee: University of Toronto Innovations Foundation, Toronto, Canada

[21] Appl. No.: 71,013

[22] Filed: Jun. 2, 1993

Related U.S. Application Data

[63] Continuation-in-part of Ser. No. 61,478, May 17, 1993.

[51] Int. Cl.$^5$ .................. C07K 15/06; C07K 3/08; C12N 9/02
[52] U.S. Cl. .................. 530/385; 435/189; 530/380; 552/577; 564/443
[58] Field of Search ............... 530/380, 385; 435/189; 552/577; 564/443

[56] References Cited

PUBLICATIONS

Song et al. "Monooxygenase–like Activity of Methemoglobin w/ Na Sulfite as an Efficient Reducant" J Am Chem Soc May 19, 1993 pp. 4365–4366.
Prez Benito et al. "Kinetics & Mechanism of the lytochrome C–Sulfite Reaction" Coll. Czech Chem Com. 56 1991 pp. 1552–1559.
Meiyal et al. "Characterization of Enzyme Like Activity of Human Hemoglobin" JBC 251 (11) 1976 pp. 3436–3441.
Fox et al. "Haloalheve Oxidatin by the Soluble Methane Monooxygenase from Methylosimus trichosprini OB3b": Mechanstic & Envirnomental impluator Biochem 29 6419–6427 1990.
Kinetics and Mechanism of the Cytochrome C–Sulfite Reaction Joaquin F. Perez–Benito et al. Collect, Czech Chem. Commun. (vol. 56) (1991) pp. 1552–1559.
Monooxygenase Activity of Human Hemoglobin: Role of Quaternary . . . Bobbe 1. Feraiolo et al. Biochemistry 1984, 23, 5528–5534.
Flavohemoglobin: A Semisynthetic Hydroxylase Acting in the Absence of Reductase, J. Am. Chem. Soc. 1987, 109, 606–607.
Characterization of Enzyme–Like Activity of Human Hemoglobin The Journal of Biological Chemistry, vol 251, No. 11, pp. 3436–3441, 1976.

Primary Examiner—Jeffrey E. Russel
Assistant Examiner—Nancy J. Gromet
Attorney, Agent, or Firm—Ridout & Maybe

[57] ABSTRACT

Oxidation of C—H bonds in organic chemical compounds to C—OH bonds is accomplished by utilizing, as a monooxygenase, a heme protein such as methemoglobin or metmyoglobin in the presence of sulfate ion, in an aqueous medium.

7 Claims, 1 Drawing Sheet

MONOOXYGENASE-LIKE ACTIVITY OF HEME PROTEINS

CROSS REFERENCE TO RELATED APPLICATION

This is a continuation-in-part of U.S. patent application Ser. No. 08/061,478, filed May 17, 1993.

FIELD OF THE INVENTION

This invention relates to protein engineering. More specifically, it relates to the use of proteins and modified proteins as catalysts in the insertion of oxygen atoms into the C—H bonds of organic compounds, i.e. as monooxygenases.

BACKGROUND OF THE INVENTION AND PRIOR ART

Cytochromes P-450, a class of cellular hemoprotein enzymes, act as monooxygenases in catalyzing metabolic functions. It fluctuates between ferrous and ferric oxidation states in acting as an electron transporter. It will catalyze the insertion of an oxygen atom into C—H bonds of organic compounds using dissolved molecular oxygen. The oxygen is cleaved, one atom inserting itself into the C—H bond and the other forming a molecule of water with hydrogen from NADPH and a reductase. The presence of iron in the cytochrome 450 renders the oxygen highly reactive.

The process is, however, limited by the availability of the protein cytochrome P-450, by the need for the presence of a reductase, and by the stoichiometric involvement of NADPH (nicotinamide-adenine dinucleotide phosphate reduced) as the reducing agent. The protein availability problem can be overcome, at least in theory, by the substitution for cytochrome P-450 of another, more readily available protein capable of exhibiting similar monooxygenase activity.

It has previously been reported that methemoglobin, a very abundant protein formed by the oxidation of hemoglobin to its ferric state, can substitute, in such C—H—C—OH bond conversions, for cytochrome P-450 in a system which utilizes NADPH as an electron source and cytochrome P-450 reductase to mediate electron transfer (Myeal et al, *J. Biol. Chem.* 1976, 251, p. 3436).

It has further been reported that a flavin-hemoglobin coupled product will function similarly and efficiently, without a reductase (Kokubo, et al, *J. Am. Chem. Soc.*, 1987, 109, p. 606)). However, the utility of both of these systems is limited by the need for the presence of NADPH, and further, in the latter case, by the complexity of the preparation of the flavin-hemoglobin coupled product.

It is an object of the present invention to provide a novel, heme protein-catalyzed process for conducting C—H—C—OH bond conversions in organic compounds having affinity for globin proteins.

It is a further object of the invention to provide such a process which does not depend on the presence in the system of the reductase and NADPH.

SUMMARY OF THE INVENTION

According to the present invention, it has been found that sodium sulfite can efficiently replace both NADPH and reductase in promoting the monooxygenase activity of a heme protein. The reaction patterns are consistent with sequential one-electron transfers with intermediate formation of the sulfite monoanion radical bound to Fe(II) hemoglobin.

Thus the present invention provides a process whereby C—H bonds in organic chemical compounds having affinity for globin proteins can be oxidized to C—OH bonds using molecular oxygen as the oxidation agent, which comprises reacting the organic chemical compound, in an aqueous medium, with dissolved molecular oxygen in the presence of a catalytically effective amount of a heme protein and sulfite ions.

BRIEF REFERENCE TO THE DRAWINGS

DESCRIPTION OF THE PREFERRED EMBODIMENTS

A wide variety of heme proteins, i.e. proteinaceous compounds containing a heme group, with the iron reversibly oxidizable and reducible between the ferrous and ferric valence states, are known and are useful in the practice of the present invention. Most preferred are hemoglobin and myoglobin, which are converted to methemoglobin and metmyoglobin in the process. Alternatively one can start with either in the meto form. The invention will be further described with reference to these heme proteins, although its application is not limited thereto.

The mechanism by which the process of the present invention proceeds appears to be one of sequential one-electron transfers with intermediate formation of the sulphite monoanion radical, bound to Fe(II) hemoglobin. Thus the catalytic process is inhibited by carbon monoxide, implicating hemoglobin-Fe(II) as an intermediate, to which carbon monoxide binds strongly, blocking the normal dioxygen activation processes. Moreover, the reaction with oxygen is not subject to inhibition by hydroxyl radical scavengers such as ethanol, mannitol and dimethylsulfoxide, in reasonable quantities. In addition, superoxide dismutase and catalase, in reasonable quantities, have no effect, indicating that superoxide and peroxide are not involved in the hydroxylation process. This is consistent with the formation of an Fe(V)=O intermediate, and the reaction scheme illustrated in FIG. 1.

The heme protein, e.g. the methemoglobin is effectively acting as a binding intermediate in electron transfer, in a sulfite complex, and splitting the oxygen molecules. The intermediate Fe(V)=O forms, to oxygenate the substrate, with the other atom of oxygen forming sulfate ion.

Figure 1:
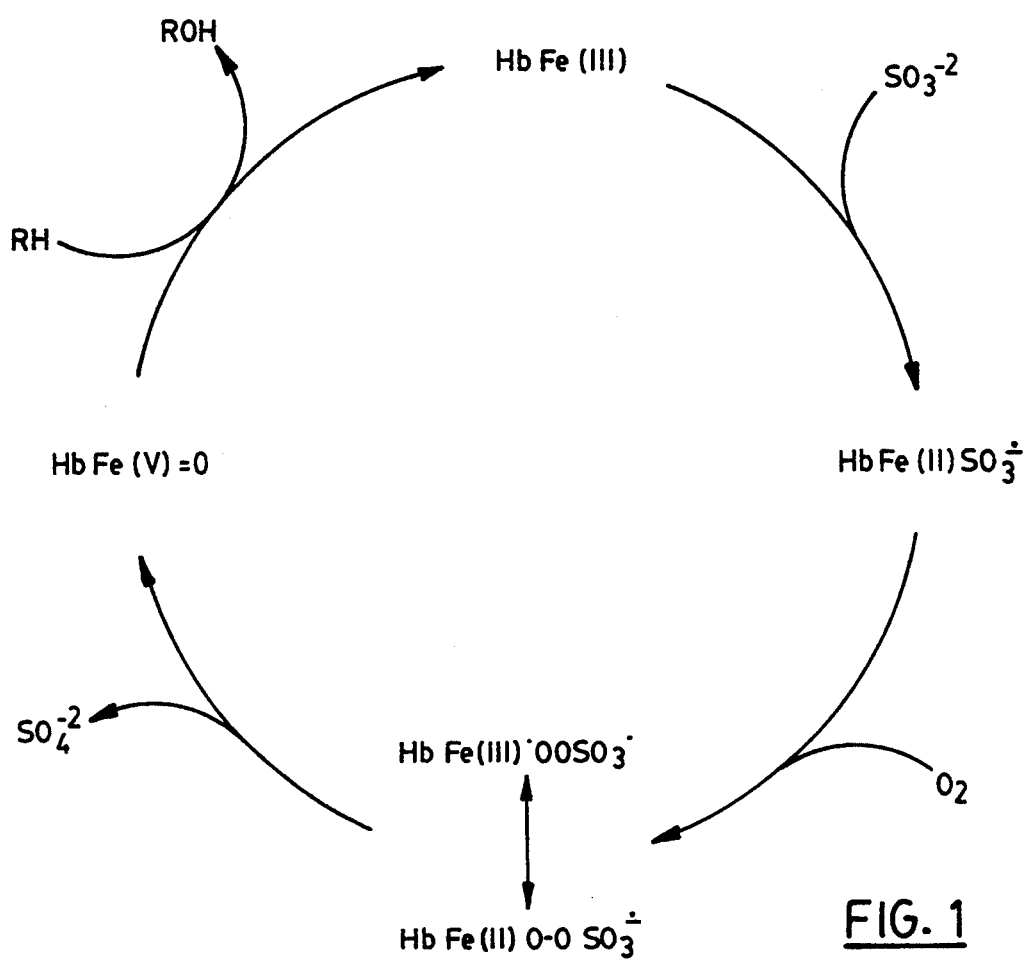
FIG. 1 is a diagrammatic scheme of the proposed reaction mechanism of process according to the invention.

The scheme illustrated in FIG. 1 of the accompanying drawings is based on analogy to the mechanisms of dioxygen activation by cytochrome P-450, the mechanism of reduction of cytochrome-c by sulfite and the kinetic and inhibition patterns discussed above and derived from the specific examples reported herein. While it is not intended that the invention should be limited to any particular theory or mechanism of reaction, it is believed that the process of the invention occurs according to the illustrated scheme.

Thus, methemoglobin, indicated as Hb Fe(III) on FIG. 1, binds sulfite to form a complex in which electron transfer gives the sulfite anion radical bound to ferrous hemoglobin, Hb Fe(II))SO3, to which oxygen then binds. This can be considered to be a resonance structure of a methemoglobin complex of peroxysulfate. Cleavage of sulfate leaves Hb(V)=O, which is believed to be the active species in oxygen insertion reactions. Oxygen is then inserted into bound substrate indicated RH on FIG. 1 to form ROH, with regeneration of methemoglobin.

The process of the present invention provides an efficient and economical method for the convenient bioactivation of C—H bonds on a wide variety of organic substrates. The source of the sulfite ion is not critical, but is conveniently provided by an alkali metal sulfite such as sodium sulfite or potassium sulfite.

The reaction is conducted in solution in an aqueous medium, so as to avoid risk of denaturing the heme protein. The range of substrates is thus limited by their ability to associate with the heme protein such as methemoglobin in an aqueous medium. Substrates which are appreciably soluble in water are thus ideally suited for use in the present invention. However, other substrates can also be successfully subjected to the oxidation process of the invention, provided that they can form a close enough association with an aqueous solution of the heme protein for effective electron transfer therebetween. This can occur, for example, at an aqueous-nonaqueous liquid phase interface, where the substrate material is essentially insoluble in water but soluble in another, water-immiscible solvent. In certain cases also, where it is desired to effect oxidation of an especially heme protein-incompatible substrate, modification of the protein portion of the heme protein, e.g. by genetic engineering, to alter its compatibility characteristics towards the particular substrate, may be undertaken. The reaction according to the invention suitably takes place at ambient temperatures. The temperature of reaction is generally not critical, provided that the stability characteristics of the various reactants and the reaction medium are respected.

In general, the process of the invention can be put to use in any of the systems for which the cytochrome P-450 monooxygenase function has previously been proposed or utilized. It can be used to oxidize hydrocarbons to chemically more useful products. When the substrate contains a plurality of C—H bonds, all of the same type, they will be oxidized sequentially, and control over the degree of oxidation of the substrate can be exercised by controlling the time of the reaction. When the substrate contains C—H bonds of different types, the selection of C—H bond for initial reaction depends upon the manner in which the substrate binds to the methemoglobin.

The source of the methemoglobin or metmyoglobin is not critical. It may be human, bovine, porcine, ovine, etc.

One specific application of the process of the present invention is in the oxidation of steroid compounds to prepare pharmaceutically useful steroids, e.g. in the oxidation of cholesterol to cortisone. Another specific application is in the treatment of oil spills, to oxidize the hydrocarbon components thereof to dispersble, less environmentally harmful products. A further specific application is in the treatment of lignin residues formed as a by-product of pulp and paper manufacture. Lignin is a dark coloured phenolic polymer, the residues of which present a particularly difficult environmental disposal problem. They can be degraded to less harmful products by oxidation of C—H bonds to C—OH bonds by the process of the present invention.

The practice of the invention is illustrated in the following specific examples. Two of the most severe tests of monooxygenase activity were chosen for these illustrative demonstration purposes, namely conversion of aniline to p-aminophenol and cleavage of anisole. Success in these two reactions is indicative to those skilled in the art of the wide range of applicability of the process of the present invention.

EXAMPLE 1

Catalysis of the conversion of aniline to p-aminophenol by methemoglobin (prepared by ferricyanide oxidation of hemoglobin) tests monooxygenase activity—see Ferraiolo et.al., *Biochemistry*, 1984, 23, 5528. In the present experiment, the conditions used were modified procedures reported by J. J. Mieyal et.al, *J. Biol. Chem.* 1976, 251, 3436-3446, the disclosure of which is herein incorporated by reference. In this assay, NADPH and NADPH-dependent P450 reductase are replaced by sodium sulphite. *Conversion of hemoglobin (Hb) to methemoglobin (MetHb)*: a solution of Mt (28 mg) in 3 ml of 20 mM $KH_2PO_4$ buffer (pH 7), [Mt] c. 0.5 mM, was oxidized to ferric form by potassium ferricyanide (4.9 mg, MW=329, 10 eq.) at room temperature for 2 hours. After the reaction, the excess potassium ferricyanide was removed by a Sephadex G-50 column. *Assay of aniline hydroxylation catalyzed by Mt*: A total volume of 0.9 mL solution containing 4.0 uM of Mt+++, 60 mM of aniline in 20 mM potassium phosphate buffer (pH 7.0) was pre-incubated at 37 degrees C. for 4-5 minutes. The reaction was then initiated by addition of 0.1 mL of 6 mM sodium sulfite, and was allowed to proceed at 37 degrees C. for another 15 minutes before it was terminated by 0.3 mL of 20% trichloroacetic acid. The resultant suspension was centrifuged for 15 minutes to remove precipitated protein and 1.0 mL of the supernatant was transferred and combined with 0.1 mL of phenol in 2.5N Na OH(w/v); after mixing, 0.2 mL of 2.5N $Na_2CO_3$ was added. The resultant mixture was allowed to stand at room temperature for 145 minutes. The optical density was measured at 630 nm against a reference sample which was obtained in such a way that incubation proceeded without Hb (or MetHb), with Met(Hb) being added after the quench with 20% trichloroacetic acid. One nmol of p-aminophenol produced in the original 1.0 mL of reaction solution gives rise to a change in absorbance at 630 nm value of 0.015.

The experiment was repeated several times, using different concentrations of sodium sulfite.

Figure 2:
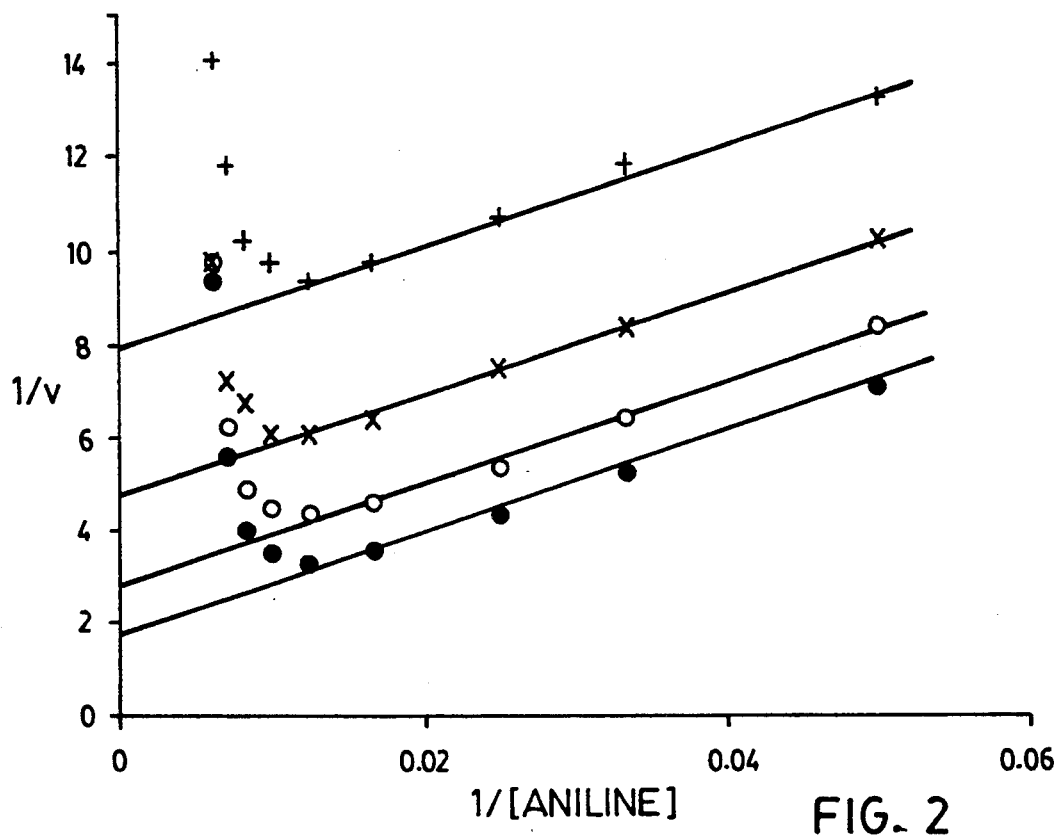
FIG. 2 is a kinetic plot derived from the results of Example 1 below.

The results are presented graphically on FIG. 2 of the accompanying drawings. These are combined Lineweaver-Burk plots of rates of p-hydroxylation of aniline (nM) as a function of sodium sulphite 0.05 mM(+), 0.10 mM(x), 0.20 mM(o) and 0.40 mM(.). Thus the reciprocal of the aniline concentration is plotted as the abscissa, against the reciprocal of the reaction rate (production of p-aminophenol, in micromoles per second), as ordinate, for the various sulphite concentrations.

The assay is linear over the 15 minute period of observation and is proportional to the methemoglobin concentration to 1.0 uM. During the assay, hemes within the protein tetramer show an unchanged Soret band, characteristic of the native protein, in contrast with reactions which produce a destructive oxidant. This indicates that the proteinaceous nature of the methemoglobin remains unchanged throughout the process.

The kinetic data obtained demonstrates that the Mt is acting in an enzyme-like, catalytic manner. As shown in FIG. 2, variation in sodium sulfite concentration produces kinetic plots indicating a ping-pong mechanism. The hydroxylation follows Michaelis-Menten kinetics with respect to aniline at constant sodium sulfite concentration.

EXAMPLE 2

An experiment was conducted exactly as described above in connection with Example 1, but using myoglobin Mb, 28 mg, MW18800, from Sigma, in place of Mt, and an amount of 0.1 mL of 6 mM sodium sulphite. Otherwise conditions and quantities were the same. An essentially similar result to that obtained with Mt in Example 1, at the same sodium sulfite amount, was obtained.

EXAMPLE 3

The cleavage of anisole is a more demanding test of monooxygenase activity—see Galaris et. al., *Arch. Biochem. Biophys.*, 1990, 281, 163 n., and Lindsay Smith et.al., *J. Chem. Soc. Chem. Commun.*, 1982, 55. GC-MS analysis of the reaction of anisole showed efficient production of phenol and formaldehyde (140 pmol/min phenol and formaldehyde). The reaction mixtures (1 mL) consisted of 20 mM potassium phosphate, pH 7.0, 2.0 Mm anisole, 1 uM methemoglobin, 0.6 mM sodium sulfite. The reaction mixtures were preincubated for 5 mins at 37 degrees C. and then terminated by addition of ice-cold 20% trichloroacetic acid (for formaldehyde determination), or by addition of ice-cold diethyl ether and subsequent extraction with diethyl ether (for GC detection of the product phenol).

What is claimed is:

1. A process whereby C—H bonds in organic chemical compounds having affinity for globin chains are oxidized to C—OH bonds, which comprises reacting the organic chemical compound in an aqueous medium containing dissolved molecular oxygen, an effective amount of a heme protein and sulfite ion, and in the absence of nicotinamide-adenine dinucleotide phosphate, reduced (NADPH), to cause splitting of the molecular oxygen followed by conversion of said C—H moieties to C—OH.

2. The process of claim 1 wherein the heme protein is methemoglobin.

3. The process of claim 1 wherein the heme protein is metmyoglobin.

4. The process of claim 1 wherein the sulfite ion is provided by addition of an alkali metal sulfite.

5. The process of claim 4 wherein the alkali metal sulfite is sodium sulfite.

6. A process of preparing HbFe(V)=O useful in oxidizing C—H bonds to C—OH bonds, which comprises cleaving a peroxymonosulfate ion $SO_5=$ from a complex of hemoglobin and sulfate symbolised as $HbFe(III)O_2SO_3$ or $HbFe(II)O_2SO_3$, in the absence of nicotinamide-adenine dinucleotide phosphate, reduced (NADPH).

7. The process of claim 6 wherein said complex is formed by reaction of a hemoglobin-sulfite complex of formula $HbFe(II)SO_3=$ with molecular oxygen in an aqueous medium, in the absence of nicotinamide-adenine dinucleotide phosphate, reduced (NADPH), to cause splitting of the molecular oxygen.

* * * * *